United States Patent [19]

Burge

[11] Patent Number: 5,708,220

[45] Date of Patent: Jan. 13, 1998

[54] LIQUID SAMPLING DEVICE AND METHOD

[76] Inventor: Russell W. Burge, 21140 Covina Hills Rd., Covina, Calif. 91724

[21] Appl. No.: 807,213

[22] Filed: Feb. 28, 1997

Related U.S. Application Data

[63] Continuation of Ser. No. 430,764, Apr. 27, 1995, abandoned.

[51] Int. Cl.$^6$ .................... G01N 1/14; E21B 49/08
[52] U.S. Cl. ...................... 73/864.34; 73/864.33; 166/264
[58] Field of Search ............. 73/864.34, 864.35, 73/864.63, 864.33; 166/264

[56] References Cited

U.S. PATENT DOCUMENTS

| | | | |
|---|---|---|---|
| 2,218,155 | 10/1940 | Rusler et al. | 73/155 X |
| 2,564,198 | 8/1951 | Elkins | 166/264 X |
| 3,113,455 | 12/1963 | Sloan et al. | 73/155 |
| 3,240,067 | 3/1966 | Jongejan | 73/864.344 X |
| 3,412,612 | 11/1968 | Carr | 73/864.34 |
| 4,295,801 | 10/1981 | Bennett | 73/864.34 X |
| 4,585,060 | 4/1986 | Bernardin et al. | 73/864.34 X |
| 4,759,227 | 7/1988 | Timmons | 73/864.34 X |
| 4,949,582 | 8/1990 | Vollweiler | 73/864.63 |
| 5,033,551 | 7/1991 | Grantom | 166/387 |
| 5,147,561 | 9/1992 | Burge et al. | 210/747 |
| 5,293,934 | 3/1994 | Burge et al. | 166/202 |
| 5,450,900 | 9/1995 | Schalla et al. | 166/264 |

FOREIGN PATENT DOCUMENTS

| | | | |
|---|---|---|---|
| 2120234 | 8/1972 | Germany | 73/864.34 |

OTHER PUBLICATIONS

CEE AutoPump advertisement of Clean Environment Equipment, Jun./Jul. 1994, p. 106, *Soils* magazine.

2-pages "Solo Pump Works" advertising material relative to a Positive Gas Displacement Pump, dated Mar. 23, 1993, Model SP4000.

*Primary Examiner*—Thomas P. Noland
*Attorney, Agent, or Firm*—Boniard I. Brown

[57] ABSTRACT

Liquid, such as ground water in a well casing, is sampled by lowering a submersible liquid sampling device to a submerged sampling position in the liquid, collecting a fixed volume sample of the liquid within a sample collection chamber in the submerged sampling device, and introducing a pressurized inert gas into the collection chamber to expel the fixed volume sample from the chamber through a sample transfer tube to a ground level sample receiver which may immediately analyze the sample or be removable for analysis of the sample in a separate laboratory.

24 Claims, 3 Drawing Sheets

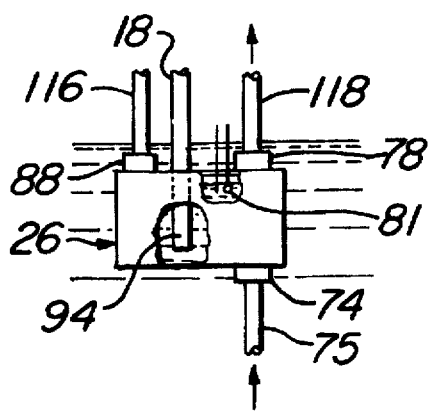
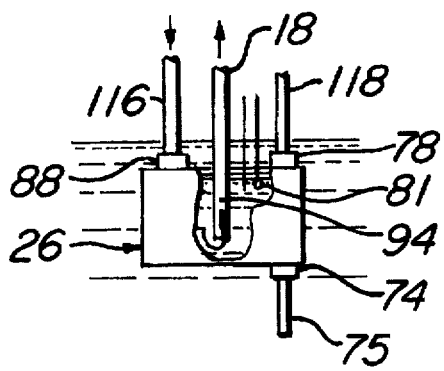
FIG.-3
FIG.-4
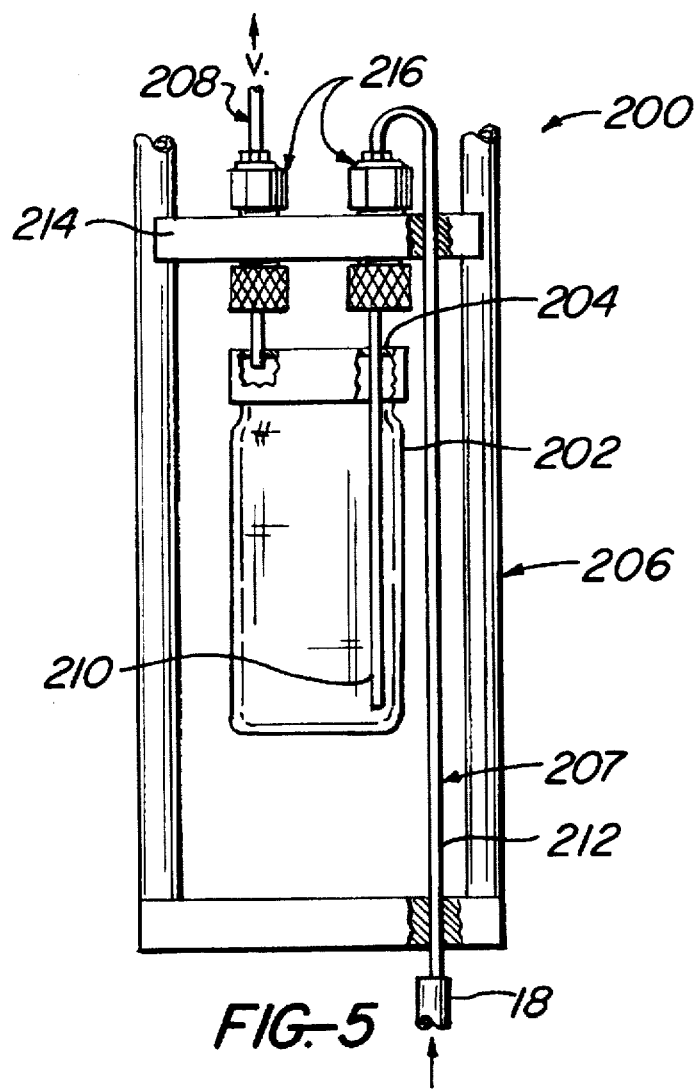
FIG.-5

LIQUID SAMPLING DEVICE AND METHOD

This application is a continuation of application Ser. No. 08/430,764 filed on Apr. 27, 1995 and now abandoned.

BACKGROUND OF THE INVENTION

1. Field of the Invention

This invention relates generally to the art of sampling liquids for analysis and more particularly to a method of and apparatus for collecting liquid samples from a body of liquid, such as ground water samples from a well bore, and transferring each sample to a sample receiving and control facility located above the surface of the liquid.

2. Discussion of the Prior Art

As will become evident from the ensuing description, the liquid sampling method and apparatus of this invention may be used to sample virtually any accessible body of liquid. The primary purpose of the sampling invention, however, is to sample liquids, particularly ground water, present in well bores and the like which open through the surface of the ground. For this reason, the invention will be described in this particular context.

Sampling ground water for analysis has become highly important because of the ever increasing concern about soil and ground water contamination by industrial chemicals and the like. The prior art is replete with a vast assortment of liquid sampling devices and systems for this and other subsurface liquid sampling purposes. Broadly speaking, the existing sampling devices for these purposes fall into three basic categories, as follows: (a) sampling devices which are lowered into a liquid to be sampled to collect a liquid sample and are then withdrawn from the liquid to retrieve the sample, (b) sampling devices which are lowered into a liquid and embody self-contained means for analyzing the liquid directly within the submerged sampling devices and transmitting the analysis data to a ground level data processing station, and (c) sampling devices which are lowered into a liquid and pump the liquid to the surface for analysis. Among the prior art disclosures of such liquid sampling devices and related devices are the following: U.S. Pat. No. 4,949,582 which falls in category (a) above; U.S. Pat. Nos. 2,564,198, 3,113,455, 5,147,561, 5,293,934 which fall into category (b) above; U.S. Pat. No. 2,218,155 which may be broadly classified in category (c) and U.S. Pat. No. 5,033,551.

The existing liquid sampling devices of the kind referred to above have certain disadvantages and deficiencies which this invention overcomes. Among the foremost of these are the following. Sampling devices of category (a) above obtain each sample by lowering the devices into the liquid to be sampled, operating the sampling devices to collect a liquid sample, withdrawing the sampling devices from the liquid, and retrieving the collected samples from the sampling devices. Obtaining each sample in this way is obviously a time consuming and tedious process. The primary disadvantage of sampling devices of category (b) above resides in the fact that containment of the sample analyzing means directly within the submersible sampling device itself necessarily restricts the accuracy and kinds of sample analyses which may be performed, exposes the analysis instrumentation to the risk of damage, unnecessarily increases the cost and complexity of the sampling device, and precludes use of such instrumentation for other purposes in an above ground laboratory. Finally, while the above mentioned U.S. Pat. No. 2,218,155 of category (c) obtains a sample from a submerged sampling device by running a swab through the pipe string while the device remains submerged, other existing ground water sampling devices which fall into category (c) generally pump the sample liquid to the surface in a manner which involves lifting a column of water equal in height to the distance from the submerged sample collection device to the surface. This obviously requires a very high pump outlet pressure, particularly if the sampling device is located a substantial distance below the surface, such as 1000 feet or more, as is often the case.

Accordingly, there is a serious need for an improved ground water sampling system and method. This invention provides a novel liquid sampling method and apparatus which is ideally suited for ground water sampling and avoids the above noted and other disadvantages and deficiencies of the existing ground water sampling systems and methods.

BRIEF DESCRIPTION OF THE INVENTION

According to one of its aspects, this invention provides an improved liquid sampling method involving lowering a sample collection chamber to a submerged sampling position in a liquid to be sampled with the collection chamber connected by a sample transfer tube to a liquid receiver located above the surface of the liquid, collecting a liquid sample of fixed volume in the submerged chamber, and utilizing fluid pressure to move this fixed volume liquid sample from the submerged collection chamber through the transfer tube to the sample receiver at the surface. The sample forms within the transfer tube a liquid column whose vertical height determines the gas pressure required to lift the column to the surface. This height of the liquid column, in turn, is determined by the fixed volume of the sample and the transfer tube diameter which are so sized that only a very low gas pressure, typically on the order of 4–5 psi, is required to raise the sample to the surface.

According to another of its aspects, this invention provides a liquid sampling apparatus for practicing the liquid sampling method of the invention. This sampling apparatus comprises, on the one hand, a submersible liquid sampling device proper to be submerged in the liquid to be sampled, and, on the other hand, a liquid sampling system including the submersible sampling device and a ground level sample receiving and control facility. Both the submersible sampling device itself and the overall liquid sampling system are operable in sample collecting and sample transfer modes. The ground level sample receiving and control facility is connected to the sampling device by control lines and fluid lines for operating the sampling device in its sample collecting and transfer modes and receiving liquid samples from the sampling device.

The submersible sampling device includes a sample collection chamber having a liquid inlet and a liquid outlet, sample collecting means for effecting inflow of a liquid sample of certain fixed volume into the chamber through the inlet during the sample collection mode, and chamber evacuation means for evacuating the collected liquid sample from the collection chamber through the outlet during the sample transfer mode. In the overall liquid sampling system of the invention this chamber outlet is connected to the ground level sample receiving and control facility by the sample transfer tube through which the sample flows from the submerged sampling device to the ground level facility during the sample transfer mode.

In the preferred sampling apparatus of the invention, liquid inflow into the collection chamber occurs by hydrostatic action. A collected sample is transferred from the sample collection chamber to the ground level facility by introducing an inert gas under pressure into the chamber to expel the sample from the chamber through the liquid transfer tube.

The surface sample receiving and control facility includes a sample receiver connected to the sampling device through the sample transfer tube and control means connected to the sampling device for operating the device in its sample collecting and transfer modes. The ground level sample receiver may itself include means for analyzing the received liquid samples directly within the receiver. Alternatively, the ground level sample receiver may be removable from the ground level sample receiving and control facility for transporting the collected sample to a laboratory for analysis. In one described embodiment of the invention, for example, the ground level fluid receiving means comprises a removable sample receiver in the form of a septum bottle and hypodermic-needle-like sample inlet and vent tubes piercing the bottle septum through which a liquid sample transferred from the submerged sampling device enters the bottle and air is vented from the bottle, respectively.

The liquid sampling method and apparatus of the invention are intended primarily for sampling ground water. The preferred liquid sampling device described herein, for example, is designed to be lowered into a well casing or the like containing ground water to be sampled. This ground water sampling device includes a well packer at its upper end which is expandable into sealing contact with the well casing to prevent volatiles in the liquid below the packer from flashing up through the well casing to the atmosphere and prevent contamination of the ground water below the packer by substances falling through the well casing. As noted earlier, and as will become evident as the description proceeds, the sampling apparatus may be used to sample other liquids than ground water and in other spaces than well bores or casings.

BRIEF DESCRIPTION OF THE DRAWINGS

FIG. 3 is a diagrammatic view illustrating the sample collection mode of the sampling system shown in FIGS. 1 and 2;

FIG. 4 is a diagrammatic view illustrating the sample transfer mode of the sampling system shown in FIGS. 1 and 2; and FIG. 5 illustrates a sample receiver which may be utilized in the sampling apparatus of FIG. 1 for receiving liquid samples at the ground level sample receiving and control facility.

DESCRIPTION OF THE PREFERRED EMBODIMENTS

Figure 1:
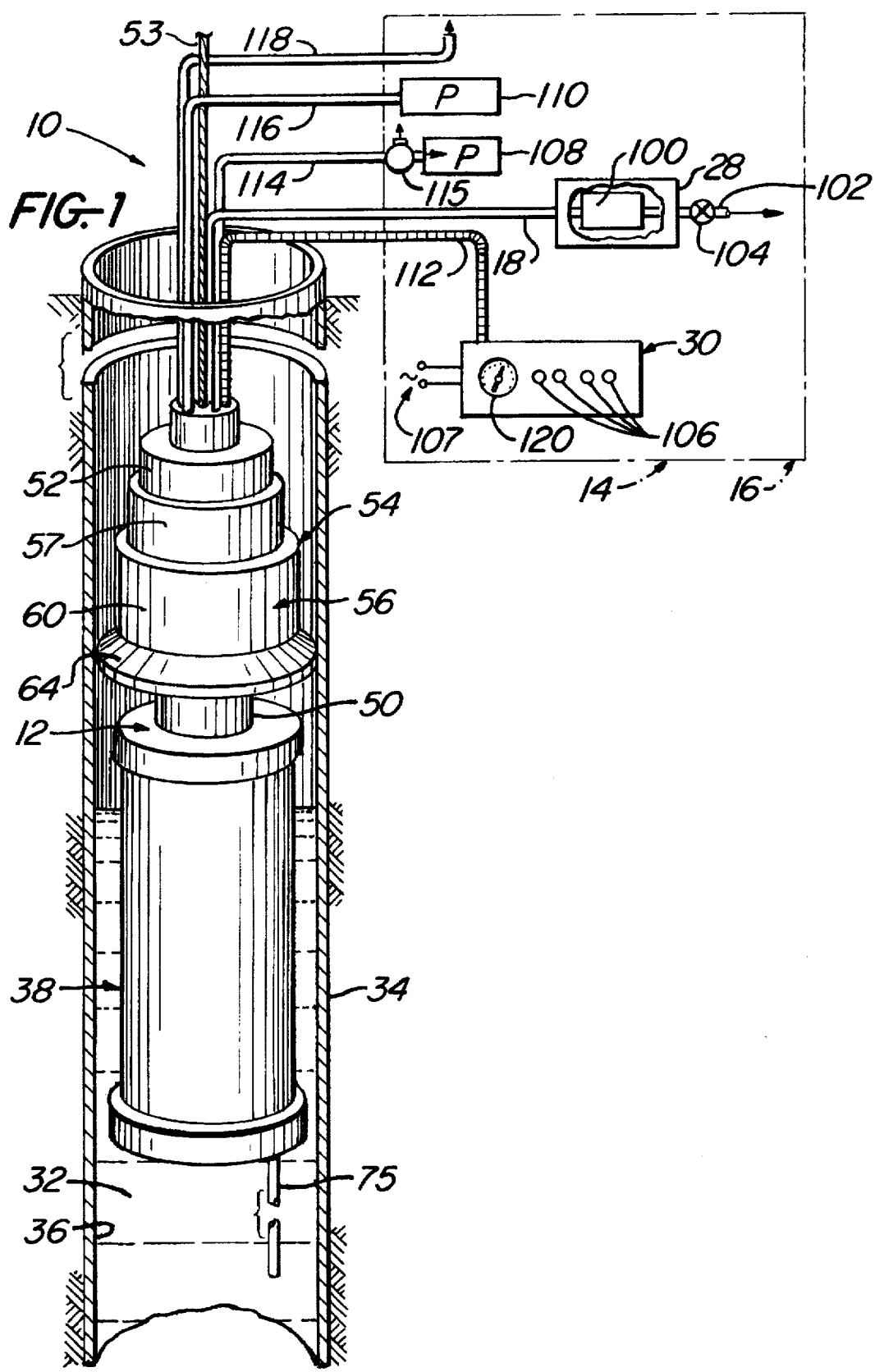
FIG. 1 is a semi-diagrammatic perspective view of a liquid sampling system according to the invention for sampling liquid, such as ground water, present in a well bore.

Referring now to these drawings, and first to FIGS. 1-4, the illustrated liquid sampling apparatus 10 of the invention includes a submersible liquid sampling device 12 proper to be lowered into liquid to be sampled and a sample receiving and control facility 14 to be located above the surface of the liquid at a ground level sample receiving site 16. This sample receiving and control facility is connected to the sampling device 12 by means including a sample transfer tube 18. The sampling device 12 and the sample receiving and control facility 14 together form a liquid sampling system. Both this sampling system and the sampling device 12 are operable in sample collecting and sample transfer modes.

The sampling device 12 comprises sample collecting means 22 and sample transfer means 24 including a common sample collection chamber 26. The sample receiving and control facility 14 includes a sample receiver 28 and control means 30 for operating the sampling device in these modes. The sample transfer tube 18 connects the sample collection chamber 26 to the sample receiver 28.

In use, the sampling device 12 is submerged in the liquid 32 to be sampled which, in this case, is ground water within the casing 34 of a well bore 36. The control means 30 at the ground level sample receiving and control facility 14 are actuated to operate the submerged sampling device 12 first in its sample collecting mode and then in its sample transfer mode. During the sample collecting mode, the sample collecting means 22 of the submerged sampling device 12 are operated to effect inflow of ground water 32 from the well casing 34 into the collection chamber 26 by hydrostatic action to provide within the chamber a water sample of certain fixed volume. During the sample transfer mode, the sample transfer means 24 are operated to transfer the collected water sample from the sample collection chamber 26 through the sample transfer tube 18 to the ground level sample receiver 28.

Referring now in more detail to the drawings, the illustrated liquid sampling device 12 has a sealed cylindrical housing 38 including a cylindrical side wall 40 sealed at its ends by upper and lower end walls 42, 44, respectively. Within the housing 38 between the end walls 42, 44 are a pair of upper and lower partitions 46, 48, respectively, securely joined to the housing side wall 40. The sample collection chamber 26 is concentrically positioned within the housing 38 between the partitions 46, 48 and is secured at its ends to the partitions.

Extending coaxially upward from the upper housing end wall 42 is a tubular housing extension 50 including a lower tubular portion 51 which is firmly threadedly joined at its lower end to the upper housing end wall 42 and a radially enlarged upper end portion 52 which is firmly threadedly joined to the upper end of the tubular portion 51. Firmly anchored to the upper end of the housing extension 50 is a hoist cable 53 by which the sampling device 12 may be lowered into and withdrawn upwardly from the liquid to be sampled.

Coaxially surrounding the housing extension 50 is a well packer or seal assembly 54 similar to the packer assembly described in U.S. Pat. No. 5,293,934. Packer assembly 54 includes a radially stepped cylindrical packer sleeve 56 coaxially surrounding the housing extension 50. The upper end portion of this packer sleeve forms a cylinder 57 which slides on and is sealed to the upper portion 52 of the housing extension 50 and is closed at its lower end by a partition wall 58. Wall 58 slides on and is sealed to the lower tubular portion 51 of the housing extension to form a cylinder space 60 between the packer sleeve 56 and the housing extension 50. Packer sleeve 56 has a lower end portion 60 which extends below the sleeve wall 58 in coaxial surrounding relation to the lower tubular portion 51 of the housing extension 50.

Coaxially fixed on the lower tubular portion 51 of the housing extension 50 is an elastic conical sealing disc 64 like that in U.S. Pat. No. 5,293,934. This sealing disc is biassed to urge the disc and the packer sleeve 56 upwardly in the drawings to their normal positions of FIG. 2 wherein the sealing disc is radially extended for sealing contact with the well casing 34. Downward movement of the sleeve against the disc effects inward radial contraction of the disc out of contact with the well casing, all in essentially the same manner as explained in U.S. Pat. No. 5,293,934.

The sample collecting means 22 of the sampling device 12 includes inlet means 68 through which ground water enters the lower end of the sample collection chamber 26 from the well casing 34 during the sample collection mode of the sampling device and vent means 70 for venting the upper end of the chamber during this mode. Inlet means 68 includes an inlet passage 72 and an inlet solenoid valve 74 for controlling flow through the passage. Inlet passage 72 has an inner end which opens to the bottom of the sample collection chamber 26 and an outer end which opens to the exterior of the sampling device through an inlet tube 75 which extends downwardly through and below the lower end wall 44 of the sampler housing 38. The collection chamber vent means 70 comprises a vent passage 76 and a solenoid vent valve 78 for controlling flow through the vent passage. Vent passage 76 has an inner end opening to the upper end of the collection chamber 26 and is contained within a vent tube 80 which extends upwardly through the upper extension 50 of the sampling device housing 38. As explained later, the inlet valve 74 and vent valve 78 are operated from the ground level sample receiving and control facility 14 during the sample collection mode of the liquid sampling device 12 to collect within the sample collection chamber 26 a ground water sample of certain fixed volume from the well casing 34. Supported within sample collection chamber 26 is a liquid level sensor 81 comprising a pair of closely positioned electrical probes for sensing the liquid level in the chamber.

The sample transfer means 24 of the sampling device 12 comprises pressurized gas inlet means 82 for introducing a pressurized inert gas, such as nitrogen, into the sample collection chamber 26 and sample outlet means 84 through which a collected liquid sample within the chamber is expelled from the chamber by the entering pressurized gas. Pressurized gas inlet means 82 includes a gas inlet passage 86 which opens at one end to the upper end of the collection chamber 26 and a solenoid valve 88 for controlling gas flow through the passage. Gas inlet passage 86 is contained with a gas supply tube 90 which extends upwardly from the collection chamber 26 through the upper extension 50 of the sampling device housing 38. The sample outlet means 84 comprise a sample outlet passage 92 which opens at one end to the lower end of the collection chamber and is contained within a sample outlet tube 94. This sample outlet tube extends upwardly from the bottom of the chamber through the housing extension 50 and connects to one end of the sample transfer tube 18. As explained later, the gas inlet valve 88 is operated from the ground level sample receiving and control facility 14 to admit inert gas under pressure into the top of the sample collection chamber 26 and thereby expel a collected ground water sample from the chamber through the outlet tube 94.

As already noted, the ground level sample receiving and control facility 14 includes a sample receiver 28 which is connected to the sampling device 12 through the sample transfer tube 18. This transfer tube has a normally lower end connected to the sample outlet tube 94 of the sampling device 12. The sample receiver 28 illustrated in FIG. 1 includes conventional sample analyzing means 100 for analyzing a sample received from the sampling device and an outlet 102 through which the sample liquid exits the receiver to a drain or the like. During use of the sampling apparatus 10, the liquid being sampled, in this case ground water, flows through the analyzing means 100 of the receiver 28 to the receiver outlet 102. This receiver outlet includes an adjustable flow rate regulating valve 104, such as a needle valve, for regulating the sample flow rate through the sample analyzing means. The valve 104 is set to prevent inert gas which enters the collection chamber 26 to expel a collected sample through the sample transfer tube 18 from "blowing through" the sample and to provide the optimum sample flow rate for the particular sample analyses being performed.

In addition to the sample receiver 28, the ground level sample receiving and control facility 14 includes the earlier mentioned control means 30 for operating the sampling device 12 in its sample collection and sample transfer modes. This ground level control means 30 includes valve operating means 106 for selectively operating the sampling device solenoid valves 61, 74, 78, 88 by selectively energizing these valves from an electrical source 107. The ground level control means 30 also includes a source 108 of packer operating fluid, such as pressurized air, and a source 110 of pressurized inert gas. The valve operating means 106 are electrically connected to the solenoid valves 61, 74, 78, 88 by electrical conductors within an electrical cable 112. The packer operating fluid source 108 is connected to the packer cylinder space 60 through a packer fluid line 114 and a fluid passage 114a in the upper portion 52 of the sampler housing extension 52. Fluid line 114 contains a valve 115 for selectively venting the fluid line 114 to atmosphere and connecting this fluid line to the packer pressure fluid source 108. The inert gas source 110 is connected to the gas inlet tube 90 of the sampling device through a gas line 116. The sampling device vent tube 80 is connected to the ground level facility 14 through a vent line 118 which opens to atmosphere at the facility. In addition to the foregoing, the ground level control means 30 include an electrical liquid level indicator 120 electrically connected by conductors in the electrical cable 112 to the liquid level sensing probes 81 in the sample collection chamber 26 of the sampling device 12 for providing an indication in response to liquid filling the chamber to the level of the sensing probes. These probes are located at a level in the chamber corresponding to a desired collected sample volume.

The operation of the present liquid sampling apparatus 10 will now be described. Valve 115 is initially positioned to connect the packer fluid line 114 to the pressure fluid source 108 to pressurize the packer cylinder space 60. The packer sleeve 56 is thereby driven downwardly against the packer sealing disc 64 to deflect this disc downward and radially inward to its retracted position. The submersible sampling device 12 is then lowered by its hoist cable 53 into the liquid to be sampled. In the case of the illustrated ground water sampling apparatus, this involves lowering the sampling device into the ground water 32 in the well casing 34 while the sealing disc 64 of the packer assembly 54 is retracted. The sampling device is thus lowered while its solenoid valves 74, 78, 88 are all closed and to a submerged sampling position in the ground water wherein the upper end of its sample collection chamber 26 is located at or below the water surface, as shown in FIG. 3. The valve 115 is then positioned to vent the packed fluid line 114 to atmosphere. This action releases the packer sealing disc 64 for radial extension by elastic strain energy in the disc and into sealing contact with the well casing 34. The sealing disc then seals off the interior of the well casing 34 below the disc to prevent flashing of volatiles present in the ground water 32 below the disc into the atmosphere, and to shield the ground water below the disc against contamination by substances falling into the well casing.

After firm setting of the packer sealing disc 64, the valve operating means 106 at the ground level sample receiving and control facility 14 are actuated to open the solenoid inlet valve 74 and the solenoid vent valve 78 of the sampling device 12. Ground water 32 then flows by hydrostatic pressure from well casing 34 into the sample collection chamber 26 through the chamber inlet passage 72 and displaces air from the chamber to atmosphere through the vent passage 76, as shown in FIG. 3. The valves 74, 78 are retained open until the liquid level indicator 120 at the ground level facility 14 indicates that the water level in the chamber has risen to the level of the sensing probes 81. At this point, the valves 74, 78 are closed to confine the collected water sample within the chamber. This collected sample has a certain fixed volume determined by the size of the collection chamber and the height of the sensing probes 81 above the bottom of the chamber. This operation constitutes the sample collection mode of the overall sampling apparatus 10 and of the sampling device 12.

The next step in the operation of the sampling apparatus is depicted in FIG. 4 and involves actuation of the ground level valve operating means 106 to open the solenoid gas valve 88 of the sampling device 12 and thereby admit pressurized inert gas from the inert gas source 110 into the top of the sample collection chamber 26. The entering inert gas displaces the fixed volume collected ground water sample from the chamber through the sample transfer tube 18 to the ground level sample receiver 28. This operation constitutes the sample transfer mode of the overall sampling apparatus 10 and the sampling device 12 and results in a water column which moves upwardly through the transfer tube to the ground level receiver.

Figure 2:
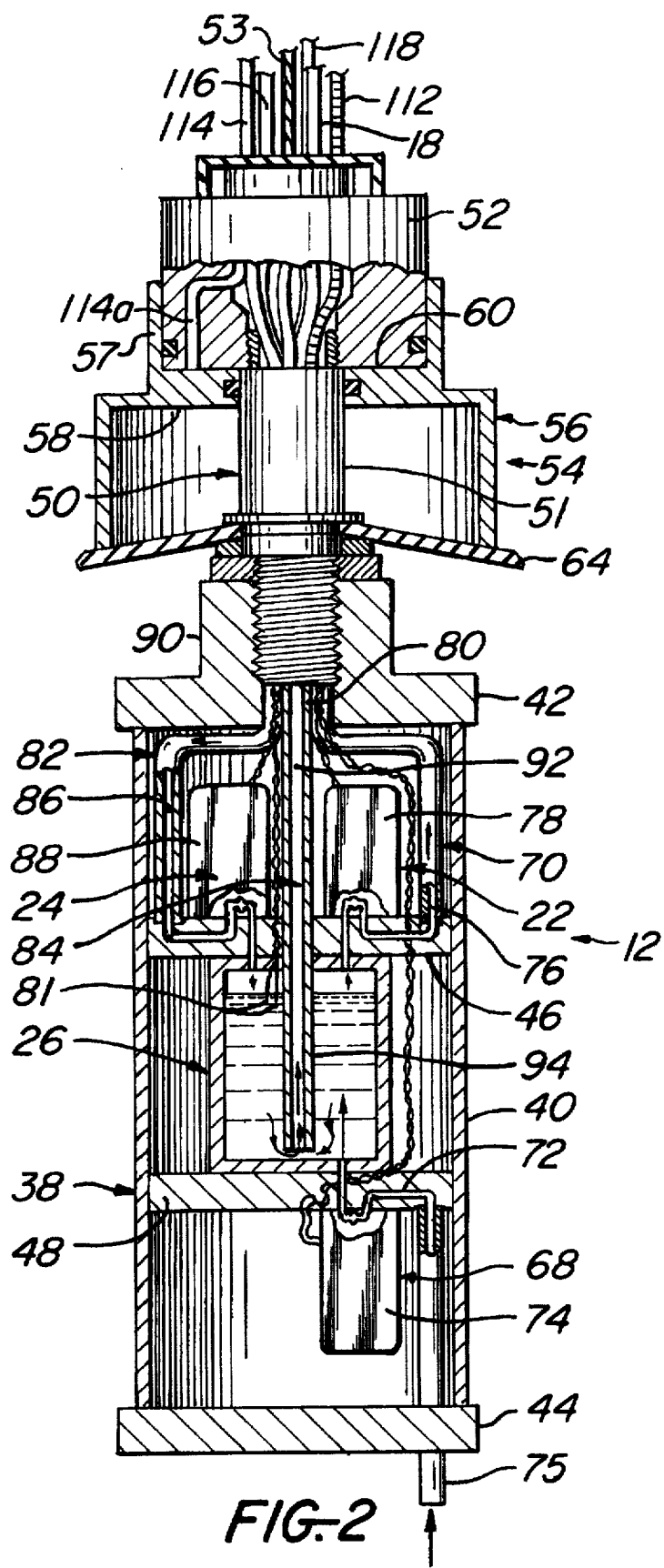
FIG. 2 is an enlarged longitudinal section through the submersible sampling device in FIG. 1.

In this regard it will be clearly seen in FIG. 2 that the present liquid sampling device is totally devoid of any barrier within the sample collection chamber 26 between the gas inlet 86 through which the pressurized gas enters the chamber and the liquid outlet 94 through which the liquid sample exits the chamber. As a consequence, pressurized gas entering the collection chamber directly contacts the liquid sample in the chamber, and continued introduction of the pressurized gas into the collection chamber through the gas inlet 86 after expulsion of the liquid sample from the chamber through the liquid outlet 94 without admission of additional liquid into the chamber, results in direct communication through the chamber of the gas inlet 86 with the liquid outlet 94 and pressurized gas flow into the liquid outlet and through the transfer tube 18 to move the liquid sample through the tube to the surface sample receiving facility 14.

A distinct advantage of the invention resides in the fact that only a fixed volume sample of ground water is transferred from the submerged sampling device 12 to the ground level sample receiving and control facility 14. This fixed sample volume is the liquid volume between the surface of the sample liquid in the collection chamber 26 and the lower open end of the liquid outlet tube 94. The inert gas pressure required to raise the liquid sample from the sampling device to the ground level facility is determined by the vertical height of the ground water column within the transfer tube 18 and hence by the interior diameter of the transfer tube and the fixed volume of the collected water sample. The sample volume is made sufficiently small to require only a very low inert gas pressure to raise the sample to the ground level receiver 28 regardless of the depth of the sampling device 12 below ground level. For example, in a typical ground water sampling apparatus system of the invention, the sample volume may be on the order of 50 ml and the interior diameter of the transfer tube 18 may be on the order of $\frac{3}{16}$ inch. The resulting transferred ground water sample passing through the transfer tube 18 forms a water column on the order of 9 inches in vertical length and requires an inert gas pressure of only about 4.2 psi to raise the sample from the submerged sampling device to the ground level sample receiving and control facility. It is obvious from the foregoing that in every actual installation of the present liquid sampling device, the length of the liquid column which is raised by gas pressure from the submerged sample collection chamber 26 to the surface sample receiving facility 14 through the transfer passage in the transfer tube 18 is substantially less than the overall length of the transfer tube itself. In this regard, it was noted earlier that liquid sampling devices (and hence the liquid sampling device of this invention) may be located 1000 feet or more below the surface, which means that the surface sample receiving facility 14 of this invention is located at a very much higher elevation than the sampling device and that the transfer tube may be 1000 feet or more in length. On the other hand, as just mentioned above, the length of the liquid column in the transfer tube may be on the order of a few inches and hence substantially less than the length of the transfer tube. This is diametrically opposed to conventional liquid sampling devices in which liquid is pumped in a continuous stream from the submerged sampling device to the surface with the result that the transfer tube and liquid column in the tube have the same length, and a very high pumping pressure is required to lift this long liquid column to the surface. The transfer tube diameter is made sufficiently small, i.e., on the order of $\frac{3}{16}$ inches, and the sample receiver valve 104 is set to prevent the gas from "blowing through" the transferring water column. The sampling device 12 remains submerged during transfer of the liquid sample so that a number of successive samples may be collected and transferred in minimum time.

FIG. 5 illustrates alternative sample receiving means 200 for the ground level sample receiving and control facility 14. Sample receiving means 200 comprises a removable sample receiver 202 in the form of a glass septum jar having a top opening closed by a septum 204. This septum jar is removably mounted on a support 206 by means of a pair of slender hypodermic-needle-like tubes 207, 208. Tube 207 is a sample inlet tube having a U-shaped bend, a free end 210 at one side of the bend and at the other side of the bend a coupling end 212 for connection to the sample transfer tube 18 extending from the submersible sampling device 12. Tube 208 is a straight vent tube. The free end 210 of the sample inlet tube 207 and the vent tube 208 extend through a normally horizontal cross member 214 of the support 206 in parallel, normally vertical side by side relation and are fixed to the cross member by clamp nuts 216. The free end 210 of the inlet tube 207 and the lower end of the vent tube 208 extend through the saprum 204 of the septum jar 202 to removably mount the jar on the support 206. The inlet tube opens to the bottom of the jar interior. The vent tube opens to the top of jar interior.

During operation of the sampling apparatus with the sample receiving means 200, a ground water sample transferred from the submerged sampling device 12 enters the bottom of the septum jar 202 through the inlet tube 207 and displaces air from the jar through the vent tube 208. After collecting a sample in the jar, the latter is removed and taken to a laboratory for analysis of the collected sample.

I claim:
1. A liquid sampling system comprising:
   a liquid sampling device to be lowered to a submerged sampling position in a body of liquid to be sampled and operable in a sample collecting mode and a sample transfer mode while in said sampling position, said sampling device comprising sample collecting means including an inlet opening to the exterior of said device and operable during said sampling collecting mode for collecting a sample of fixed volume of the liquid in which the device is submerged, and sample transfer means including a liquid outlet opening externally of said device and operable during said sample transfer mode for evacuating a sample from said device through said outlet, sample receiving means to be located at a sample receiving site remote from sampling device, a sampling transfer tube connecting said outlet of said sampling device to said sampling receiving means, control means to be located at said sample receiving site and connected to said sampling collecting means and said sample transfer means for operating said sample collecting means and said sample transfer means to collect in said sampling device a sampling of fixed volume of the liquid in which the sampling device is submerged and then transfer the collected sample to said remote sample receiving means through said sample transfer tube, and wherein said sample receiving means comprises a removable sample container, said sample container comprises a septum bottle having a top opening and a septum closing said top opening, said sample receiving means further comprises a support, a pair of tubular needles mounted on said support including a first needle having open ends and a second having one end connected to said sample transfer tube for receiving liquid from said liquid sampling device and an opposite free end, and said needles puncture said septum for connecting said bottle to said liquid sampling device to receive a liquid sample from said liquid sampling device through one needle and vent the bottle to atmosphere through the other needle.

2. A liquid sampling system comprising:

a liquid sampling device to be lowered below ground level to a submerged sampling position in a body of liquid to be sampled and operable in a sample collecting mode and in a sample transfer mode while in said sampling position, said sampling device comprising sample collecting means including a sample collection chamber having a liquid inlet opening to the exterior of said device and a liquid outlet, sample collecting means operable in said sample collecting mode for effecting entrance of liquid in which the device is submerged into said collecting chamber through said inlet to collect within the chamber a liquid sample having a fixed volume, and sample transfer means operable in said sample transfer mode for evacuating a said liquid sample from said collection chamber through said outlet, sample receiving means to be located at a ground level sample receiving site remote from said sampling device, a sample transfer tube connecting said outlet of said sampling device to said sample receiving means, and control means to be located at said sample receiving site and connected to said sample collecting means and said sample transfer means for operating said sample collecting means and said sample transfer means to collect a liquid sample of said fixed volume in said sample collection chamber and then transfer the collected sample from said chamber to said remote sample receiving means, and wherein said chamber has normally upper and lower ends, said outlet opens to said chamber adjacent the lower end of the chamber, said sample collecting means includes a vent tube having one end connected to the upper end of said chamber and an opposite end to be located at said sample receiving site for venting said chamber to atmosphere during entrance of liquid into said chamber during said sample collection mode, said chamber evacuating means includes a pressurized gas source to be located at said sample receiving site and a gas tube having one end connected to said gas source and its opposite end connected to the upper end of said chamber for introducing pressurized gas into said chamber to expel a liquid sample from said chamber through said sample transfer tube, said sample receiving means comprises a removable sample container, said sample container comprises a septum bottle having a top opening and a septum closing said top opening, said sample receiving means further comprises a support, a pair of tubular needles mounted on said support including a first needle having open ends and a second having one end connected to said sample transfer tube for receiving liquid from said liquid sampling device and an opposite free end, and said needles puncture said septum for connecting said bottle to said liquid sampling device to receive a liquid sample from said liquid sampling device through one needle and vent the bottle to atmosphere through the other needle.

3. Liquid sampling apparatus for sampling liquid in a body of liquid and operable in a sample collecting mode and in a sample transfer mode, said sampling device comprising:

a sampling device to be lowered to a submerged sampling position in said body of liquid and including a sample collection chamber having upper and lower ends, a liquid inlet opening into said chamber and to the exterior of said device for inflow of liquid from said body of liquid into said chamber through said inlet, a pressurized gas inlet opening into said chamber, and a liquid outlet opening into said chamber adjacent the lower end of the chamber and to the exterior of said device, sample collecting means for affecting inflow of liquid in which said sampling device is submerged into said collection chamber through said liquid inlet in said sample collecting mode to collect within the chamber a liquid sample having a certain fixed liquid volume and then closing said liquid inlet to block further liquid inflow into the chamber and liquid outflow from said chamber through said liquid inlet, sample transfer means for introducing a pressurized gas into said chamber through said gas inlet in said sample transfer mode and while said liquid inlet is closed to expel said liquid sample from said collection chamber through said outlet, and wherein said sampling device is devoid of any barrier blocking direct communication through said chamber between said gas inlet and said outlet, and said sample transfer means is operable to continue introducing pressurized gas into said chamber through said gas inlet drier expulsion of the entire liquid sample from the chamber through said outlet and without admission of additional liquid into the chamber, whereby Pressurized gas entering the chamber after expulsion of the liquid sample from the chamber exits the chamber through said outlet.

4. Liquid sampling apparatus according to claim 3 wherein:

said sample transfer means includes a sample transfer passage opening at one end to said outlet and extending externally of said sampling device for conducting the liquid sample from said outlet to a remote sample receiving site, said transfer passage receives the fixed volume liquid sample from said collection chamber through said outlet and forms the liquid sample into a liquid column within the transfer passage having a certain finite length which is inversely proportional to the diameter of the transfer passage, directly proportional to the fixed volume of the liquid sample, and substantially less than the length of the transfer passage, and pressurized gas introduced into said chamber after expulsion of the liquid sample from the chamber through said transfer passage enters the transfer passage behind said liquid column and moves the liquid column though the entire length of said transfer passage.

5. Liquid sampling apparatus according to claim 3 wherein:

said sample collecting means includes vent means including a vent passage opening to said chamber at the upper end of the chamber for venting said chamber through said vent passage during entrance of liquid into the chamber through said liquid inlet in said sample collecting mode, and means for closing said vent passage during introduction of pressurized gas into said chamber in said sample transfer mode.

6. Liquid sampling apparatus according to claim 5 wherein:

said vent passage extends externally of said device for venting said chamber to atmosphere above the liquid in which said device is submerged during said sample collection mode.

7. Liquid sampling apparatus according to claim 3 wherein:

said means for introducing a pressurized gas into said chamber comprises a pressurized gas source, a gas passage connecting said source to said gas inlet for conducting pressurized gas from said pressurized gas source to said chamber, a gas valve for controlling gas flow from said source into said chamber through said gas passage, and means for operating said gas valve to continue introducing pressurized gas into said chamber through said gas inlet after expulsion of the entire liquid sample from the chamber through said outlet, whereby pressurized gas entering the chamber after expulsion of the liquid sample from the chamber exits the chamber through said outlet.

8. Liquid sampling apparatus according to claim 7 wherein:

said sample collecting means includes an inlet valve for controlling flow through said inlet, and means for operating said inlet valve, said vent means comprises a vent valve for controlling flow through said vent passage, and means for operating said vent valve, said sample transfer means comprises an outlet valve for controlling flow through said outlet, and means for operating said gas valve and said outlet valve, and said means for operating said valves include means for retaining said inlet valve and vent valve closed and said gas valve and outlet valve open after expulsion of the entire liquid sample from the chamber through said outlet so as to continue introducing pressurized gas into said chamber after expulsion of the entire liquid sample from the chamber through said outlet, whereby pressurised gas entering the chamber after expulsion of the liquid sample from the chamber exits the chamber through said outlet.

9. Liquid sampling apparatus according to claim 8 wherein:

said valves comprise electrically operated valves, and said liquid sampling apparatus includes means for operating said valve from a remote control site.

10. Liquid sampling apparatus according to claim 3 wherein:

said sample collecting means comprises vent means including a vent passage opening at one end to the upper end of said chamber and extending externally of said device for venting the upper end of said chamber in said sample collecting mode to atmosphere above the liquid in which said device is submerged during said sample collection mode, said sample transfer means comprises a sample transfer passage opening at one end to said outlet and extending externally of said device for conducting the liquid sample from said outlet to a remote sample receiving site above the liquid in which said device is submerged, said transfer passage receives the liquid sample through said outlet and forms the liquid sample into a liquid column within the transfer passage, and said fixed volume of said liquid sample and the diameter of said transfer passage are such that said liquid column has a certain finite length which is inversely proportional to the diameter of the transfer passage, directly proportional to the fixed volume of the liquid sample, and substantially less than the length of the transfer passage, and pressurized gas introduced into said chamber after expulsion of the liquid sample from the chamber through said transfer passage enters the transfer passage behind said liquid column and moves the liquid column though the entire length of said transfer passage.

11. Liquid sampling apparatus according to claim 3 wherein:

said sample collecting means comprises an inlet valve for controlling liquid flow through said liquid inlet, vent means including a vent passage extending externally of said sampling device and having one end opening to the upper end of said chamber and an opposite end opening to atmosphere for venting the upper end of said chamber to atmosphere above the liquid in which said device is submerged during said sample collecting mode, a vent valve in said vent passage, and means for operating said valves, and said sample transfer means includes a gas valve for controlling pressurized gas flow into said chamber through said gas inlet, an outlet valve for controlling liquid flow through said outlet, and means for operating said gas valve and said outlet valve, and said means for operating said valves include means for retaining said inlet valve and vent valve closed and said gas valve and outlet valve open after expulsion of the entire liquid sample from the chamber through said outlet so as to continue introducing pressurized gas into said chamber after expulsion of the entire liquid sample from the chamber through said outlet, whereby pressurized gas entering the chamber after expulsion of the liquid sample from the chamber exit the chamber through said outlet.

12. Liquid sampling apparatus operable in a sample collecting mode and a sample transfer mode, comprising:

a sampling device to be lowered to a submerged sampling position in a body of liquid to be sampled and including a sample collection chamber having upper and lower ends, a liquid inlet opening into said chamber and to the exterior of said device for inflow of liquid from said body of liquid into said chamber through said inlet, a liquid outlet opening into said chamber adjacent the lower end of the chamber and to the exterior of said device through which liquid may be expelled from said chamber, a gas inlet opening into said chamber and to the exterior of device through which a pressurized gas may be introduced into said chamber, and a vent opening into said chamber and to the exterior of said device through which said chamber may be vented to ambient atmosphere, and electrically actuated remotely operable valves for selectively controlling flow through said liquid inlet, said liquid outlet, said gas inlet, and said vent.

13. A liquid sampling system operable in a sample collecting mode and a sample transfer mode, said system comprising:

a liquid sampling device to be submerged in a liquid to be sampled and including a sample collection chamber having upper and lower ends, a liquid inlet opening into said chamber and to the exterior of said device for inflow of liquid in which said device is submerged into said chamber through said inlet, a pressurized gas inlet opening into said chamber, and a liquid outlet opening into said chamber adjacent the lower end of the chamber and to the exterior of said device, sample receiving means to be located at a sample receiving site above the liquid in which said device is submerged, a sample transfer passage connecting said outlet to said sample receiving means, sample collecting means operable in said sample collecting mode for admitting liquid in which said device is submerged into said collection chamber through said liquid inlet to collect within the chamber a liquid sample having a certain fixed volume and then closing said inlet to block further liquid inflow into said chamber through said inlet and liquid outflow from said chamber through said liquid inlet, sample transfer means for introducing a pressurized gas into said chamber through said gas inlet in said sample transfer mode to expel the liquid sample from said collection chamber through said outlet and said transfer passage, control means to be located at said sample receiving site and connected to said sample collecting means and said sample transfer means for operating said collecting means and transfer means, and wherein said device is devoid of any barrier which blocks direct communication between said inlet and outlet through said chamber after expulsion of the entire liquid sample from the chamber through said outlet, and said sample transfer means is operable to continue introducing pressurized gas into said chamber after expulsion of the entire liquid sample from the chamber through said outlet and without admission of additional liquid into the chamber, whereby pressurized gas entering the chamber after expulsion of the liquid sample from the chamber exits the chamber through said outlet and said transfer passage, said transfer passage receives the liquid sample from said chamber through said outlet and forms the sample into a liquid column having a certain finite length which is directly proportional to the fixed volume of the sample, inversely proportional to the diameter of said transfer passage, and substantially less than the length of said transfer passage, and control means to be located at said sample receiving site and connected to said sample collecting means and said sample transfer means for operating said sample collecting means to collect a liquid sample of said fixed liquid volume within said chamber and then operating said sample transfer means without admission of more liquid into the chamber to introduce pressurized gas into the chamber through said gas inlet in a manner such that the gas first expels the collected sample of fixed volume from said chamber through said outlet into said transfer passage and then enters the transfer passage behind the liquid column formed by the liquid sample within said transfer passage and pushes the liquid column through the transfer passage to said sample receiving means.

14. A liquid sampling system according to claim 13 wherein:

said sample receiving means comprises a removable sample container.

15. A liquid sampling system according to claim 14 wherein:

said sample container comprises a septum bottle having a top opening and a septum closing said top opening, said sample receiving means further comprises a support, a pair of tubular needles mounted on said support including a first needle having open ends and a second having one end connected to said sample transfer tube for receiving liquid from said liquid sampling device and an opposite free end, and said needles puncture said septum for connecting said bottle to said liquid sampling device to receive a liquid sample from said liquid sampling device through one needle and vent the bottle to atmosphere through the other needle.

16. A liquid sampling system according to claim 13 wherein:

said sample receiving means includes liquid analyzing means through which the liquid sample flows.

17. A liquid sampling system according to claim 16 wherein:

said sample receiving means includes valve means for regulating the flow rate of the liquid sample through said liquid analyzing means.

18. A liquid sampling system according to claim 13 wherein:

said sample collecting means comprises a vent passage opening at one end to said chamber and extending externally of said device for venting said chamber to atmosphere above the liquid in which said device is submerged during said sample collection mode, and a vent valve operable from said sample receiving site for closing said passage during said sample transfer mode.

19. A liquid sampling system according to claim 13 wherein:
said means for introducing a pressurized gas into said chamber comprises a pressurized gas source, a gas tube containing a gas passage connecting said source and said gas inlet for conducting pressurized gas from said pressurized gas source to said chamber, a gas valve for controlling gas flow through said gas passage, and means for operating said valves from said sample receiving site.

20. A liquid sampling system according to claim 13 wherein:
said sample collecting means comprises an inlet valve for controlling liquid flow through said liquid inlet, vent means including a vent valve for venting the upper end of said chamber to atmosphere above the liquid in which said device is submerged during said sample collecting mode, and means for operating said valves from said sample receiving site, and
said sample transfer means includes a gas valve for controlling gas flow through said gas inlet, an outlet valve for controlling flow through said outlet, and means for operating said gas valve and said outlet valve from said sample receiving site.

21. Liquid sampling apparatus according to claim 13 wherein:
said sample collecting means includes an inlet valve for controlling flow through said liquid inlet, a vent tube containing a vent passage opening to the upper end of said chamber and extending externally of said device for venting said chamber to atmosphere above the liquid in which said device is submerged, a vent valve for controlling flow through said vent passage, and means for operating said inlet valve and said vent valve from said sample receiving site, and
said sample transfer means comprises a gas valve for controlling gas flow through said gas inlet, an outlet valve for controlling flow through said outlet, and means for operating said gas valve and said outlet valve from said sample receiving site.

22. A liquid sampling system according to claim 21 wherein:
said valves comprise electrically operated valves.

23. A liquid sampling installation comprising:
a body of liquid to be sampled located below ground level,
liquid sampling apparatus operable in a sample collecting mode and a sample transfer mode and comprising a liquid sampling device including a sample collection chamber having upper and lower ends, means supporting said sampling device in a submerged sampling position in said liquid, a liquid inlet opening into said chamber and to the exterior of said device, a liquid outlet opening into said chamber adjacent the lower end of the chamber and to the exterior of said sampling device, sample receiving means located at a ground level sample receiving site, and a liquid transfer passage connecting said liquid outlet to said liquid receiving means, and wherein
said sampling apparatus further comprises sample collecting means operable in said sample collecting mode for effecting inflow of said liquid into said collection chamber through said inlet to collect within said chamber a liquid sample having a certain fixed volume and then closing said inlet to block liquid inflow into and liquid outflow from said chamber through said inlet and sample transfer means for introducing a pressurized gas into said chamber in said sample transfer mode and while said inlet is closed to expel the liquid sample from said chamber through said outlet and said transfer passage, and said device is devoid of any barrier which blocks direct communication between said inlet and outlet through said chamber after the liquid sample has been expelled from said chamber,
said sample transfer passage receives the liquid sample from said chamber through said outlet and forms the sample into a liquid column in said transfer passage having a certain finite length which is directly proportional to the fixed volume of the sample, inversely proportional to the diameter of said transfer passage, and substantially less than the length of said transfer passage, and
said sampling apparatus further includes control means located at said sample receiving site and connected to said sample collecting means and said sample transfer means for first operating said sample collecting means to collect said liquid sample within said chamber and then close said liquid inlet and thereafter operating said sample transfer means while said inlet is closed and hence without admission of additional liquid into the chamber to introduce into the chamber a pressurized gas which first expels the collected sample of fixed volume from said chamber through said outlet into said transfer passage and then enters said transfer passage behind the liquid column formed by the liquid sample within said transfer passage and moves the liquid column through the transfer passage to said sample receiving means.

24. A liquid sampling method comprising the steps of:
providing a liquid sampling apparatus including a sampling device containing a sample collection chamber having upper and lower ends for receiving a liquid sample of a certain fixed liquid volume, a liquid inlet opening to said chamber and to the exterior of said device, a liquid outlet opening to said chamber adjacent the lower end of the chamber and to the exterior of said device, a gas inlet opening to said chamber, and wherein said sampling device is devoid of any barrier blocking direct communication between said gas inlet and said liquid outlet, whereby gas entering said gas inlet may exit said chamber through said liquid outlet, a sample receiver, and a sample transfer passage connecting said outlet to said sample receiver having a diameter such that a liquid sample of said fixed liquid volume contained within said passage is formed into a liquid column having a certain finite length which is directly proportional to the said liquid volume, inversely proportional to said diameter, and substantially less than the length of said passage,
placing said device in a submerged sampling position within a body of liquid to be sampled located below ground level,
placing said sample receiver at a sample receiving site located above said liquid,
admitting liquid into said chamber through said liquid inlet from
said body of liquid to provide within said chamber a liquid sample of said certain fixed liquid volume and then closing said liquid inlet, and
while said device occupies said submerged sampling position with said liquid inlet closed introducing into said chamber through said gas inlet a pressurized gas which first expels said fixed volume liquid sample from said chamber through said outlet into said sample transfer passage to form a liquid column of said certain length within the passage and then enters said passage behind said liquid column to move said liquid column through said passage to said sample receiver.

* * * * *